(12) United States Patent
Fathollahi

(10) Patent No.: US 10,543,056 B2
(45) Date of Patent: Jan. 28, 2020

(54) MOUNT FOR REDUNDANT FLAT-SCREEN MONITORS USED IN MEDICAL IMAGING APPLICATIONS

(71) Applicant: Ampronix, Inc., Irvine, CA (US)

(72) Inventor: Nausser Fathollahi, Irvine, CA (US)

(73) Assignee: Ampronix, Inc., Irvine, CA (US)

( * ) Notice: Subject to any disclaimer, the term of this patent is extended or adjusted under 35 U.S.C. 154(b) by 0 days.

(21) Appl. No.: 15/648,676

(22) Filed: Jul. 13, 2017

(65) Prior Publication Data

US 2018/0014905 A1 Jan. 18, 2018

Related U.S. Application Data

(60) Provisional application No. 62/361,721, filed on Jul. 13, 2016.

(51) Int. Cl.
| | |
|---|---|
| *A61B 90/00* | (2016.01) |
| *F16M 13/02* | (2006.01) |
| *F16M 11/20* | (2006.01) |
| *F16M 11/08* | (2006.01) |
| *H04N 5/655* | (2006.01) |
| *H04N 5/63* | (2006.01) |

(Continued)

(52) U.S. Cl.
CPC ............ *A61B 90/37* (2016.02); *F16M 11/08* (2013.01); *F16M 11/2085* (2013.01); *F16M 13/027* (2013.01); *H04N 5/268* (2013.01); *H04N 5/63* (2013.01); *H04N 5/655* (2013.01); *H04N 7/183* (2013.01); *A61B 2090/372* (2016.02); *A61B 2090/373* (2016.02); *A61B 2562/227* (2013.01); *G06F 3/1423* (2013.01)

(58) Field of Classification Search
CPC .... A61B 90/37; F16M 11/08; F16M 11/2085; F16M 11/425; F16M 13/027; G06F 3/1423; H04N 5/63; H04N 5/655; H04N 7/183
See application file for complete search history.

(56) References Cited

U.S. PATENT DOCUMENTS

| | | | | |
|---|---|---|---|---|
| 5,856,819 A | * | 1/1999 | Vossler | ............ G09F 9/35 345/102 |
| 2004/0195471 A1 | * | 10/2004 | Sachen, Jr. | ............ F16M 11/10 248/127 |

(Continued)

*Primary Examiner* — John R Schnurr
(74) *Attorney, Agent, or Firm* — George Fountain; Loza & Loza LLP (57) ABSTRACT

A mount is described herein for supporting first and second flat-screen monitors. The mount includes a mounting member with first and second opposing sides, wherein the first and second sides includes first and second power connectors and first and second video connectors for mating with corresponding first and second power connectors and corresponding first and second video connectors of the first and second flat-screen monitors, respectively. The mount further includes first and second power buses for supplying power to the first and second flat-screen monitors via the first and second power connectors. Additionally, the mount includes a video bus for supplying a video signal to the first and second flat-screen monitors via the first and second video connectors. The mount also includes a supporting member mechanically coupled to or integral with the mounting member for supporting the mount on a fixed structure.

20 Claims, 4 Drawing Sheets

(51) Int. Cl.
*H04N 7/18* (2006.01)
*H04N 5/268* (2006.01)
*G06F 3/14* (2006.01)

(56) References Cited

U.S. PATENT DOCUMENTS

| | | | | |
|---|---|---|---|---|
| 2006/0132594 | A1* | 6/2006 | Parsons | A61G 15/10 348/14.01 |
| 2006/0187140 | A1* | 8/2006 | Brask | G06F 1/1601 345/1.1 |
| 2007/0052683 | A1* | 3/2007 | Knott | G06F 1/1601 345/173 |
| 2016/0381813 | A1* | 12/2016 | Jeon | H05K 5/0017 361/752 |

* cited by examiner

MOUNT FOR REDUNDANT FLAT-SCREEN MONITORS USED IN MEDICAL IMAGING APPLICATIONS

CROSS-REFERENCE TO RELATED APPLICATION

This application claims the benefit of the filing date of U.S. Provisional Application, Ser. No. 62/361,721, filed on Jul. 13, 2016, which is incorporated herein by reference.

FIELD

Aspects of the present disclosure relate generally to medical imaging systems, and more particularly, to a mount for redundant flat-screen monitors used in medical imaging applications.

BACKGROUND

Medical imaging monitors are often employed to provide imaging information (e.g., video and/or still images) of a patient undergoing a medical procedure to one or more medical personnel. Such imaging information may include information concerning vitals of a patient, such as heart rate, blood pressure, electrocardiogram, etc. Additionally, such imaging information may also include x-rays, medical resonance imaging (MRI), etc. Often, such monitor displays multiple screens (e.g., split screen) depicting separate imaging information of a patient.

As the use of such medical imaging monitors may be critical to a medical procedure being performed on a patient, such a monitor failing during the procedure may be dangerous to the patient. Accordingly, it would be safer if redundant medical imaging monitors are accessible to medical personnel during medical procedures being performed on patients. Furthermore, the redundant monitors should be accessible in a manner that swapping a failed monitor for a redundant monitor may be easily performed in a relatively fast manner so as to minimize disruption of the medical procedure being performed on the patient.

SUMMARY

The following presents a simplified summary of one or more embodiments in order to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of one or more embodiments in a simplified form as a prelude to the more detailed description that is presented later.

An aspect of the disclosure relates to a mount for supporting at least first and second flat-screen monitors. The mount includes a mounting member including at least first and second sides, wherein the at least first and second sides include first and second power connectors and first and second video connectors for mating with corresponding first and second power connectors and corresponding first and second video connectors of the first and second flat-screen monitors when the first and second flat-screen monitors are securely mounted to the first and second sides of the mounting member, respectively.

The mount further includes first and second power buses for supplying power to the first and second flat-screen monitors via the first and second power connectors of the at least first and second sides of the mounting member and the corresponding first and second power connectors of the first and second flat-screen monitors, respectively; a video bus for supplying a video signal to the first and second flat-screen monitors via the first and second video connectors of the at least first and second sides of the mounting member and the corresponding first and second video connectors of the first and second flat-screen monitors, respectively; and a supporting member mechanically coupled to or integral with the mounting member for supporting the mount on a fixed structure.

To the accomplishment of the foregoing and related ends, the one or more embodiments include the features hereinafter fully described and particularly pointed out in the claims. The following description and the annexed drawings set forth in detail certain illustrative aspects of the one or more embodiments. These aspects are indicative, however, of but a few of the various ways in which the principles of various embodiments may be employed and the description embodiments are intended to include all such aspects and their equivalents.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, well-known structures and components are shown in block diagram form in order to avoid obscuring such concepts.

This disclosure relates to a mount for supporting redundant flat-screen monitors, which facilitates swapping a failed monitor with a redundant monitor in an easy and rapid manner. The mount is described below with reference to various figures.

Figure 1A:
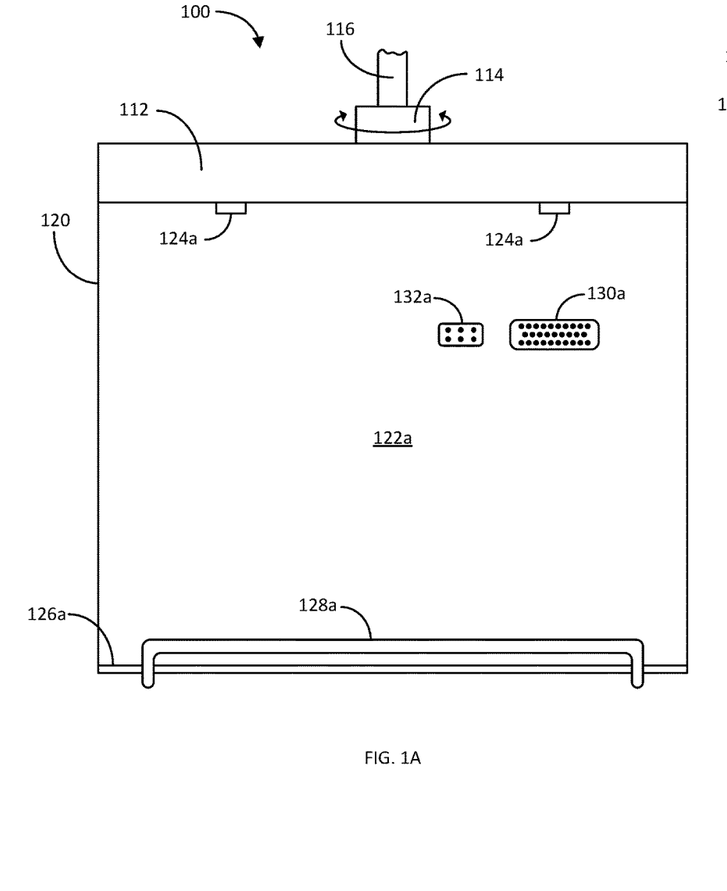
FIGS. 1A-1B illustrate front and side views of an exemplary mount for redundant flat-screen monitors in accordance with an aspect of the disclosure.
Figure 1B:
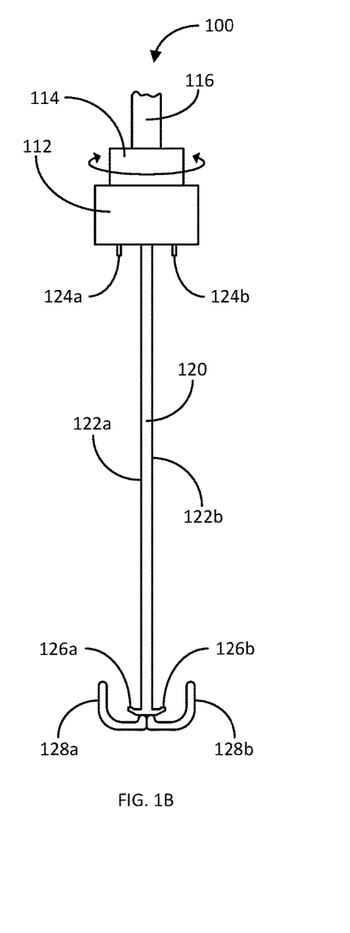

FIGS. 1A-1B illustrate front and side views of an exemplary mount 100 for redundant flat-screen monitors in accordance with an aspect of the disclosure. The mount 100 includes a horizontal supporting member 112 configured to support a flat mounting member 120 in a substantially vertical manner More specifically, the bottom of the horizontal supporting member 112 is mechanically coupled to or integral with a top of the flat mounting member 120 in a substantially longitudinal, parallel, and laterally aligned manner.

The horizontal supporting member 112 is also mechanically coupled to or integral with a bore or bearing member 114. The bearing member 114 is rotationally coupled to a lower end of a substantially vertical supporting rod 116, as indicated by the rotational arrows depicted. The vertical supporting rod 116 may include an upper end fixed to a stationary or horizontally rolling or sliding ceiling member (See FIGS. 3A-3B). This allows the mount 100 to hang down from the ceiling member. Accordingly, because of the bearing member 114, the horizontal angular position of the mount 100 may be adjusted. Furthermore, if the ceiling member is able to slide horizontally, the lateral position of the mount 100 may also be adjusted.

The flat mounting member 120 includes a first opposing side 122a for receiving a first flat-screen monitor 200a (shown in FIGS. 2A-2C) in a substantially flushed manner. The bottom of the horizontal supporting member 112 (on the first opposing side 122a) includes a pair of spaced-apart flexible tabs 124a configured to secure the first flat-screen monitor 200a on the first opposing side 122a of the flat mounting member 120. Additionally, the flat mounting member 120 includes, proximate its bottom end on the first opposing side 122a, a first lip 126a upon which a bottom portion of the first flat-screen monitor 200a rests or is supported.

Figure 2A:
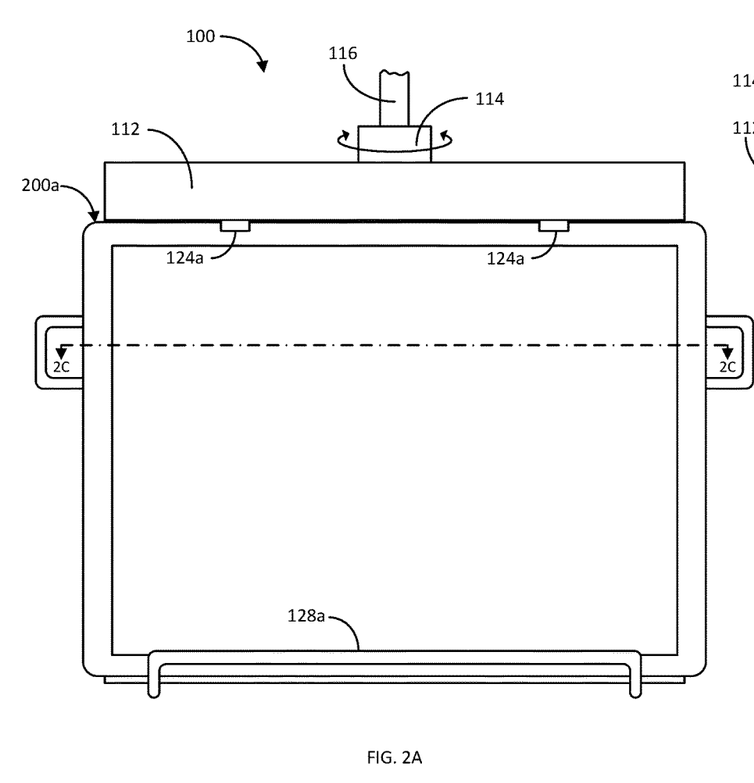
FIGS. 2A-2B illustrate front and side views of the exemplary mount supporting redundant flat-screen monitors in accordance with another aspect of the disclosure.
Figure 2B:
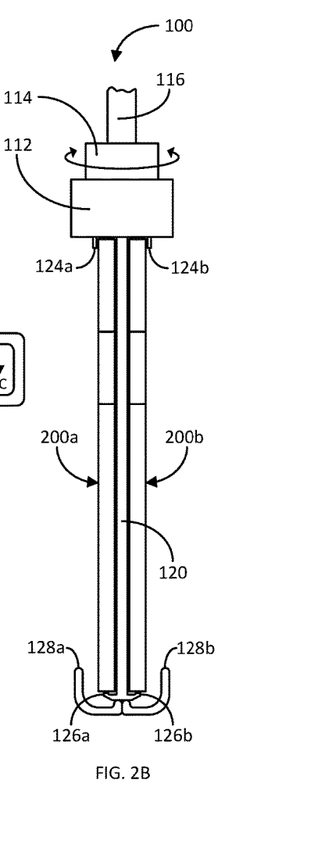

As illustrated in FIGS. 2A-2B, when properly mounted, the top of the of the first flat-screen monitor 200a is substantially flushed with the bottom of the horizontal supporting member 112 between the tabs 124a and the first opposing side 122a of the flat mounting member 120. The bottom of the first flat-screen monitor 200a sits substantially flushed on the first lip 126a. The back side of the first flat-screen monitor 200a is substantially flushed with the first opposing side 122a of the flat mounting member 120. Thus, the first flat-screen monitor 200a is securely mounted on the first opposing side 122a of the flat mounting member 120 by being seated flushed on the lip 126a at its bottom and sandwiched between the tabs 124a and the first opposing side 122a at its top.

Similarly, the flat mounting member 120 further includes a second opposing side 122b for receiving a second flat-screen monitor 200b (shown in FIGS. 2A-2C) in a substantially flushed manner. The bottom of the horizontal supporting member 112 (on the second opposing side 122b) includes a pair of spaced-apart flexible tabs 124b configured to secure the second flat-screen monitor 200b on the second opposing side 122b of the flat mounting member 120. Additionally, the flat mounting member 120 includes, proximate its bottom end on the second opposing side 122b, a second lip 126b upon which a bottom portion of the second flat-screen monitor 200b rests or is supported.

As illustrated in FIGS. 2A-2B, when properly mounted, the top of the second flat-screen monitor 200b is substantially flushed with the bottom of the horizontal supporting member 112 between the tabs 124b and the second opposing side 122b of the flat mounting member 120. The bottom of the first flat-screen monitor 200b sits substantially flushed on the second lip 126b. The back side of the second flat-screen monitor 200b is substantially flushed with the second opposing side 122b of the flat mounting member 120. Thus, the second flat-screen monitor 200b is securely mounted on the second opposing side 122b of the flat mounting member 120 by being seated flushed on the lip 126b at its bottom and sandwiched between the tabs 124b and the second opposing side 122b at its top.

The mount 100 further includes first and second opposing rails 128a and 128b for facilitating the positioning (laterally and rotationally) of the mount. In particular, the first opposing rail 128a includes a horizontal member positioned centrally a small distance in front of the first opposing side 122a and extending horizontally almost to the full width of the flat mounting member 120. The first opposing rail 128a includes a pair of attaching portions secured to the bottom of the flat mounting member 120. As illustrated in FIGS. 2A-2B, when properly mounted, the bottom portion of the first flat-screen monitor 200a is situated between the horizontal member of the first opposing rail 128a and the first opposing side 122a of the flat mounting member 120.

Similarly, the second opposing rail 128b includes a horizontal member positioned centrally a small distance in back of the second opposing side 122b and extending horizontally almost to the full width of the flat mounting member 120. The second opposing rail 128b includes a pair of attaching portions secured to the bottom of the flat mounting member 120. As illustrated in FIGS. 2A-2B, when properly mounted, the bottom portion of the second flat-screen monitor 200b is situated between the horizontal member of the second opposing rail 128b and the second opposing side 122b of the flat mounting member 120.

Figure 2C:
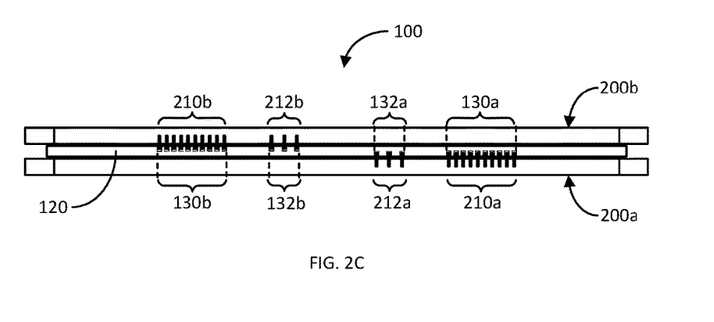
FIG. 2C illustrates a cross-sectional view of the exemplary mount along line 2C-2C of FIG. 2A in accordance with another aspect of the disclosure.

For providing imaging information (video and/or still-images) and power (alternating current (AC) and/or direct current (DC) voltages) to the first flat-screen monitor 200a, the first opposing side 122a of the flat mounting member 120 includes a video connector 130a and a power connector 132a. As illustrated in FIG. 2C, the first flat-screen monitor 200a includes, on its back side, a corresponding video connector 210a and a corresponding power connector 212a. When the first flat-screen monitor 200a is properly mounted on the first opposing side 122a of the flat mounting member 120, the video connector 210a and the power connector 212a of the first flat-screen monitor 200a mate with the video connector 130a and the power connector 132a on the first opposing side 122a of the flat mounting member 120, respectively.

Similarly, for providing imaging information and power to the second flat-screen monitor 200b, the second opposing side 122b of the flat mounting member 120 includes a video connector 130b and a power connector 132b. As illustrated in FIG. 2C, the second flat-screen monitor 200b includes, on its back side, a corresponding video connector 210b and a corresponding power connector 212b. When the second flat-screen monitor 200b is properly mounted on the second opposing side 122b of the flat mounting member 120, the video connector 210b and the power connector 212b of the second flat-screen monitor 200b mate with the video connector 130b and the power connector 132b on the second opposing side 122b of the flat mounting member 120, respectively.

Figure 1C:
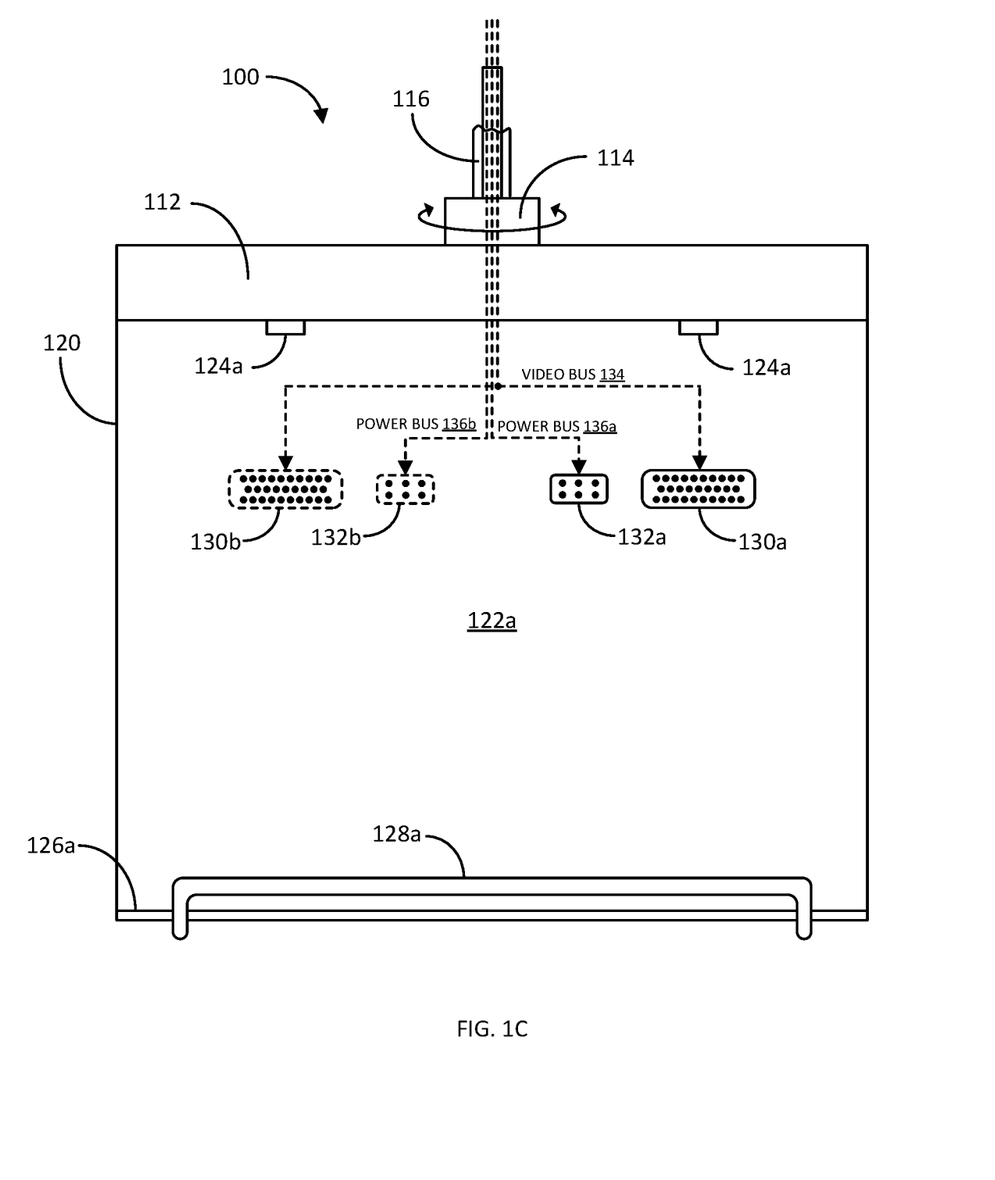
FIG. 1C illustrates a front internal view of the exemplary mount for redundant flat-screen monitors in accordance with another aspect of the disclosure.

As illustrated in FIG. 1C, the mount 100 includes a video bus 134 for routing the same video signal to the video connectors 130a and 130b. Similarly, the mount 100 includes a first power bus 136a for routing power to the power connector 132a. Additionally, the mount 100 includes a second power bus 136b for routing power to the power connector 132b. The video bus 134 and the first and second power buses 136a and 136b may be respectively routed from above the ceiling to the video connectors 130a and 130b and the power connectors 132a and 132b via an internal longitudinal channel within the vertical supporting rod 116, and internal channels within the horizontal supporting member 112 and the flat mounting member 120.

Figures 3A, 3B:
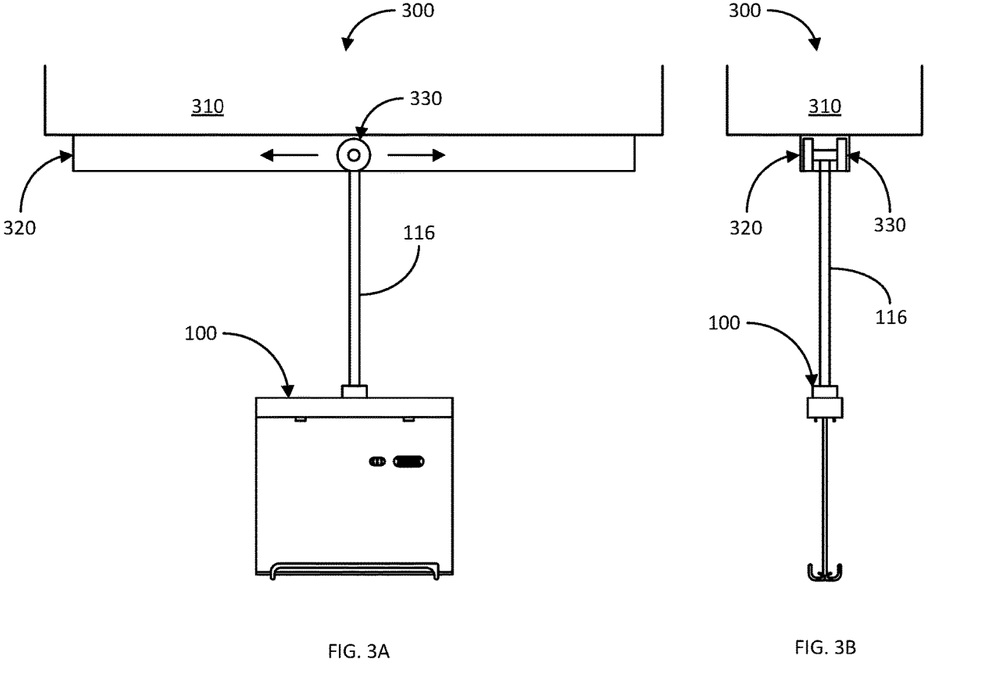
FIGS. 3A-3B illustrates front and side view of an exemplary monitor mount system in accordance with another aspect of the disclosure.

Thus, a user, such as medical personnel, may mount the redundant monitors 200a and 200b on the first and second opposing sides 122a and 122b of the mount 100, respectively. Power is supplied to the monitors 200a and 200b via the first and second power buses 136a and 136b and power connectors 132a/212a and 132b/212b, respectively. The same video signal is supplied to the monitors 200a and 200b via the video bus 134 and the video connectors 130a/210a and 130b/210b, respectively. Accordingly, if one of the monitors fails during a medical procedure being performed on a patient, a user may simply rotate the mount 100 to view the other redundant monitor and continue performing the medical procedure on the patient in a safe manner FIGS. 3A-3B illustrates front and side view of the exemplary monitor mount system 300 in accordance with another aspect of the disclosure. The monitor mount system 300 includes the mount 100 with the vertical supporting rod 116 mechanically coupled to and supported by a ceiling member 310.

In particular, the monitor mount system 300 includes a horizontal track 320 mounted on the ceiling member 310. A roller unit 330 (or sliding unit) is configured to roll (or slide) along the horizontal track 320 as indicated by the accompanying arrows. The roller unit 330 is mechanically attached to or integral with the vertical supporting rod 116. Thus, a user may grab either rail 128a or 128b of the mount 116, and move the mount 116 horizontally (laterally) to orient the monitors 200a and 200b as desired, whereby the roller unit 330 moves along the horizontal track 320. In addition to the horizontal movement, the user may also rotate the mount 100 with respect to the vertical supporting rod 116 to angularly orient the monitors 200a and 200b as desired.

Figure 4:
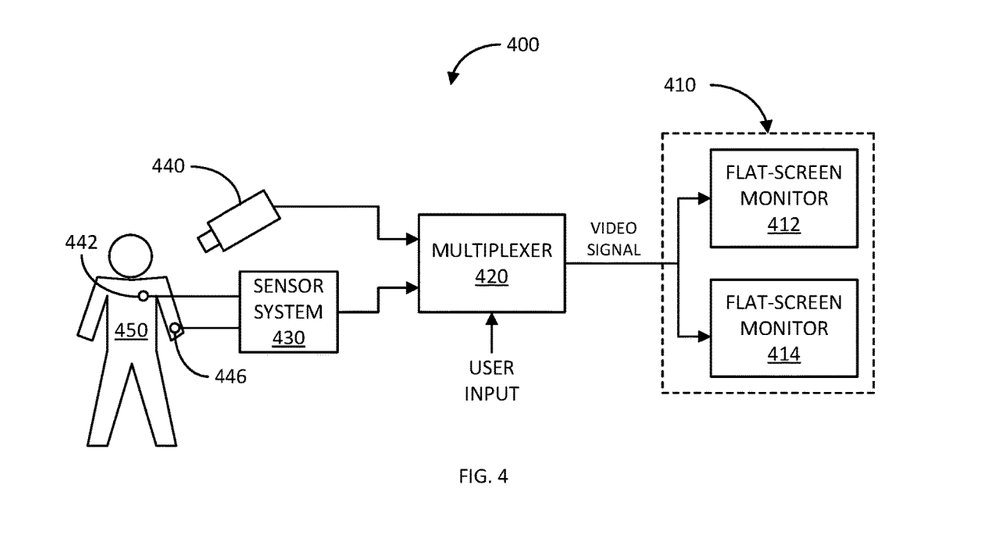
FIG. 4 illustrates a block diagram of an exemplary medical imaging system in accordance with another aspect of the disclosure.

FIG. 4 illustrates a block diagram of an exemplary medical imaging system 400 in accordance with another aspect of the disclosure. The medical imaging system 400 includes a mount 410 (such as the mount 100 previously discussed), and a pair of flat-screen monitors 412 and 414 supported on the mount 410 as previously discussed.

The medical imaging system 400 includes one or more medical monitoring devices, such as an imaging device 440 (e.g., a camera, x-ray unit, medical resonance imaging (MRI) unit, etc.), and a sensor system 430 (e.g., electrocardiogram unit, blood pressure monitoring unit, etc.) including one or more sensors 442 and 446 disposed on and/or near a patient 450. The imaging device 440 and sensor system 430 generate respective video signals.

The medical imaging system 400 includes a multiplexer 420 configured to receive the video signals from the one or more medical monitoring devices 430 and 440, and generate a video signal based on one or more of the video signals from the one or more medical monitoring devices 430 and 440 and a user input. As an example, the multiplexer 420 may output only the video signal from the sensor system 430 based on the user input. Alternatively, the multiplexer 420 may output only the video signal from the imaging device 440 based on the user input. Alternatively, the multiplexer 420 may output a composite video signal based on the video signals from both the sensor system 430 and the imaging device 440 based on the user input. The composite video signal may produce split screen images on each of the flat-screen monitors 412 and 414.

The video signal generated by the multiplexer 420 is sent to the flat-screen monitors 412 and 414 via the video bus of the mount 410 as previously discussed. As the flat-screen monitors 412 and 414 function as redundant monitors used in a medical procedure setting, the same video signal is applied to the flat-screen monitors 412 and 414 such that they both are capable of producing redundant video and/or image based on the video signal. Of course, one of the flat-screen monitors 412 and 414 may be turned off while the other is being used to display the video and/or image.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples described herein but is to be accorded the widest scope consistent with the principles and novel features disclosed herein.

What is claimed is:

1. A mount for supporting first and second flat-screen monitors, comprising:
    a single-flat mounting member including first and second opposite sides, wherein the first and second opposite sides include first and second power connectors and first and second video connectors for mating with corresponding first and second power connectors and corresponding first and second video connectors of the first and second flat-screen monitors when the first and second flat-screen monitors are securely mounted by an end-user to the first and second opposite sides of the mounting member, respectively;
    first and second power buses for supplying power to the first and second flat-screen monitors via the first and second power connectors of the first and second opposite sides of the single-flat mounting member and the corresponding first and second power connectors of the first and second flat-screen monitors, respectively;
    a video bus for supplying an identical video signal to the first and second flat-screen monitors via the first and second video connectors of the first and second opposite sides of the single-flat mounting member and the corresponding first and second video connectors of the first and second flat-screen monitors, respectively; and
    a supporting member mechanically coupled to or integral with the single-flat mounting member for supporting the mount on a fixed structure.

2. The mount of claim 1, wherein the single-flat mounting member includes at least one internal channel within the power bus and the video bus are routed to the first and second power connectors and the first and second video connectors, respectively.

3. The mount of claim 1, further comprising a horizontal supporting member including a bottom mechanically coupled to or integral with a top of the single-flat mounting member.

4. The mount of claim 3, further comprising:
    a first set of one or more tabs extending downward from the bottom of the horizontal supporting member and spaced apart from the first side of the single-flat mounting member, wherein a space between the first set of one or more tabs and the first side of the single-flat mounting member is configured to receive a top portion of the first flat-screen monitor; and
    a second set of one or more tabs extending downward from the bottom of the horizontal supporting member and spaced apart from the second side of the single-flat mounting member, wherein a space between the second set of one or more tabs and the second side of the single-flat mounting member is configured to receive a top portion of the second flat-screen monitor.

5. The mount of claim 3, further comprising a bore mechanically coupled to or integral with a top of the horizontal supporting member, wherein the supporting member comprises a vertical supporting rod including a lower portion thereof rotationally coupled to the bore and a top portion configured to mechanically coupled to the fixed structure.

6. The mount of claim 5, wherein the fixed structure comprises a ceiling member, and wherein the top portion of the vertical supporting rod is configured to move horizontally along a track mounted to the ceiling member.

7. The mount of claim 5, further comprising at least one internal channel extending longitudinally within the vertical supporting rod, within the horizontal supporting member, and within the single-flat mounting member, through which the power bus and video bus are routed to the first and second power connectors and the first and second video connectors, respectively.

8. The mount of claim 1, further comprising:
a first lip attached to or integral with a lower portion of the single-flat mounting member, wherein the first lip is configured to support the first flat-screen monitor from a bottom thereof; and
a second lip attached to or integral with the lower portion of the single-flat mounting member, wherein the second lip is configured to support the second flat-screen monitor from a bottom thereof.

9. A medical imaging system, comprising:
a first flat-screen monitor;
a second flat-screen monitor;
a single-flat mounting member including a first side upon which the first flat-screen monitor is supported when mounted thereon by an end-user, and a second side upon which the second flat-screen monitor is supported when mounted thereon by the end-user, wherein the first and second opposite sides respectively include first and second power connectors and first and second video connectors mated with corresponding first and second power connectors and corresponding first and second video connectors of the first and second flat-screen monitors, respectively;
first and second power buses for supplying power to the first and second flat-screen monitors via the first and second power connectors of the first and second opposite sides of the single-flat mounting member and the corresponding first and second power connectors of the first and second flat-screen monitors, respectively;
a video bus for supplying an identical video signal to the first and second flat-screen monitors via the first and second video connectors of the first and second opposite sides of the single-flat mounting member and the corresponding first and second video connectors of the first and second flat-screen monitors, respectively; and
a supporting member mechanically coupled to or integral with the single-flat mounting member for supporting the mount on a fixed structure.

10. The medical imaging system of claim 9, wherein the single-flat mounting member includes at least one internal channel within the power bus and video bus are routed to the first and second power connectors and the first and second video connectors, respectively.

11. The medical imaging system of claim 9, further comprising a horizontal supporting member including a bottom mechanically coupled to or integral with a top of the single-flat mounting member.

12. The medical imaging system of claim 11, further comprising:
a first set of one or more tabs extending downward from the bottom of the horizontal supporting member and spaced apart from the first side of the single-flat mounting member, wherein a top portion of the first flat-screen monitor is situated between the first set of one or more tabs and the first side of the single-flat mounting member; and
a second set of one or more tabs extending downward from the bottom of the horizontal supporting member and spaced apart from the second side of the single-flat mounting member, wherein a top portion of the second flat-screen monitor is situated between the second set of one or more tabs and the second side of the single-flat mounting member.

13. The medical imaging system of claim 11, further comprising a bore mechanically coupled to or integral with a top of the horizontal supporting member, wherein the supporting member comprises a vertical supporting rod including a lower portion thereof rotationally coupled to the bore and a top portion mechanically coupled to the fixed structure.

14. The medical imaging system of claim 13, wherein the fixed structure comprises a ceiling member, and wherein the top portion of the vertical supporting rod is configured to move horizontally along a track mounted to the ceiling member.

15. The medical imaging system of claim 13, further comprising at least one internal channel extending longitudinally within the vertical supporting rod, within the horizontal supporting member, and within the single-flat mounting member, through which the power bus and video bus are routed to the first and second power connectors and the first and second video connectors, respectively.

16. The medical imaging system of claim 9, further comprising:
a first lip attached to or integral with a lower portion of the single-flat mounting member, wherein a lower portion of the first flat-screen rests upon the first lip; and
a second lip attached to or integral with the lower portion of the single-flat mounting member, wherein a lower portion of the second flat-screen rests upon the second lip.

17. The medical imaging system of claim 9, further comprising at least one rail attached to or integral with a lower portion of the single-flat mounting member, wherein the at least one rail facilitates a user in orienting the mount.

18. A medical imaging system, comprising:
at least one medical monitoring device configured to generate at least one video signal including information regarding a patient undergoing a medical procedure;
a first flat-screen monitor;
a second flat-screen monitor;
a single-flat mounting member including a first side upon which the first flat-screen monitor is supported when mounted thereon by an end-user, and a second side upon which the second flat-screen monitor is supported when mounted thereon by the end-user, wherein the first and second opposite sides include first and second power connectors and first and second video connectors mated with corresponding first and second power connectors and corresponding first and second video connectors of the first and second flat-screen monitors, respectively;
first and second power buses for supplying power to the first and second flat-screen monitors via the first and second power connectors of the first and second opposite sides of the single-flat mounting member and the corresponding first and second power connectors of the first and second flat-screen monitors, respectively;

a video bus for routing an identical output video signal, based on the at least one input video signal, to the first and second flat-screen monitors via the first and second video connectors of the first and second opposite sides of the single-flat mounting member and the corresponding first and second video connectors of the first and second flat-screen monitors, respectively; and a supporting member mechanically coupled to or integral with the single-flat mounting member for supporting the mount on a fixed structure.

19. The medical imaging system of claim 18, wherein the at least one medical monitoring device comprises a set of medical monitoring devices, and wherein the at least one input video signal comprises a set of input video signals, respectively.

20. The medical imaging system of claim 19, further comprising a multiplexer configured to generate the output video signal based on the set of input video signals.

\* \* \* \* \*